United States Patent [19]

Carnes et al.

[11] 4,185,093

[45] Jan. 22, 1980

[54] PREPARATION AND METHOD FOR TREATMENT OF HYPOCALCEMIA, HYPOPHOSPHATEMIA AND DOWNER COW SYNDROME IN ANIMALS

[76] Inventors: Allen R. Carnes, 313 W. 2nd St.; Douglas D. Mann, RFD 3, both of New Richmond, Wis. 54017

[21] Appl. No.: 916,947

[22] Filed: Jun. 19, 1978

Related U.S. Application Data

[63] Continuation of Ser. No. 815,492, Jul. 14, 1977, abandoned.

[51] Int. Cl.$^2$ .................. A61K 33/14; A61K 33/06; A61K 31/19
[52] U.S. Cl. .................................. 424/153; 424/154; 424/317
[58] Field of Search .................. 424/153, 154, 317

[56] References Cited

PUBLICATIONS

U.S. Dispensatory, 25th Edition (1955), pp. 1954 and 1955.
Veterinary Drug Encyclopedia, 12th Edition (1964), p. 32.

*Primary Examiner*—Sam Rosen
*Attorney, Agent, or Firm*—Williamson, Bains, Moore & Hansen

[57] ABSTRACT

The invention relates to pharmaceutical preparations comprising calcium lactate, calcium chloride and calcium levulinate. The solutions contain 7 to 28 grams of calcium ion with 10% to 30% of the calcium provided from calcium chloride, 20% to 60% from calcium lactate, and 20% to 60% from calcium levulinate and serves as an effective treatment for hypocalcemia, hypophosphatemia and downer cow syndrome.

12 Claims, No Drawings

PREPARATION AND METHOD FOR TREATMENT OF HYPOCALCEMIA, HYPOPHOSPHATEMIA AND DOWNER COW SYNDROME IN ANIMALS

This application is a continuation of our application bearing Ser. No. 815,492, filed July 14, 1977 and now abandoned.

The present invention relates to therapeutic calcium electrolytic solutions for intravenous administration in ruminant animals suffering with the clinical signs or pathology of hypocalcemia, hypophosphatemia and downer cow syndrome. These conditions describe what is commonly known as "milk fever".

In ruminant animals, the occurance of hypocalcemia has several profound effects. Physically, paresis is exhibited in varying degrees ranging from ataxia to paraplegia. Clinical pathology of the serum of these animals reveals significant decreases in serum calcium, serum phosphorus, and declining insulin levels. Simultaneously, the serum magnesium and serum glucose levels climb to abnormal highs.

Traditional treatment has consisted of the administration of calcium salts intravenously, subcuteanously or intramuscularly. Examples of these treatments are calcium salts such as calcium chloride, calcium gluconate, calcium borogluconate, calcium hypophosphite, calcium lactate, calcium glycerophosphate, calcium levulinate used either alone or in combination or with salts of magnesium, potassium, phosphites and glucose. Examples of preparations previously tried are given in U.S. Pat. Nos. 2,140,291 and 3,553,148.

Calcium chloride, while providing a rapid response in the patient animals, has potential for toxicity and acute heart block if administered too rapidly or in too concentrated a solution. Perivascular administration results in tissue necrosis.

Calcium borogluconate has the disadvantage of containing boron which is noted for its toxic effect on hepatic tissue making this salt, although widely used, less than good therapy.

Calcium hypophosphite is proclaimed as a source of both calcium and phosphorus. However, studies have shown that the hypophosphite, in addition to being a strong reducing agent, is excreted in the urine, biologically unchanged and unutilized.

Certain combinations of calcium salts in suspension have been tried, i.e. calcium lactate and calcium glycerophosphate. This combination contains insufficient calcium to be effective by recommended intermuscular administration.

The addition of magnesium salts to these solutions is contraindicated since hypocalcemic ruminants already have an elevated serum magnesium level.

The addition of glucose to calcium solutions is unacceptable. In order for the body to use glucose, it must utilize phosphorus from the serum thus aggravating the pre-existing hypophosphatemia. When serum phosphorus levels drop low enough, a serious shift in the oxyhemoglobin occurs which can result in tissue anoxia with brain, hepatic and erythrocyte damage.

It is an object of this invention to provide a new combination of calcium salts containing calcium chloride, calcium lactate and calcium levulinate. This is a clear, stable, aqueous solution.

An important advantage of the present invention is to provide therapeutic solutions which produce a rapid rate of therapeutic response in the patient. A further important advantage is to provide such solutions which provide a high level of continuing effectiveness after administration. Further important advantages of the invention are the provision of therapeutic electrolytic solutions having very low toxicity and lowered irritability. The solutions also have the advantage of stability and ease of induction. Another advantage is the presence in the solution of calcium lactate which provides a vehicle for potential buffer formation thus avoiding undesirable PH variations.

Calcium chloride, when used as 10% to 30% of the calcium ion source in such combination of ingredients provides a more rapid recovery without the previously noted toxicity effects.

The calcium lactate supplying 20% to 60% of the calcium ion source, also provides the lactate fraction which may be converted to biocarbonate. This may provide a buffering capability to the solutions which restores the ruminant's base deficit that exists in hypocalcemia and hypophosphatemia.

The calcium levulinate is an excellent source for 20% to 60% of the calcium ions. Because it is non-irritating, it dilutes the irritating effect of the lactate and chloride salts.

The foregoing and related objects of the invention can be achieved by preparing an aqueous solution containing from 7 to 28 grams of dissolved calcium ion per 500 cc's of solution in the form of a water soluable mixture of calcium chloride, calcium lactate and calcium levulinate. Such solutions have been found effective in formulations wherein 10% to 30% of the dissolved calcium ion is provided by calcium chloride, 20% to 60% thereof by calcium lactate and 20% to 60% thereof by calcium levulinate.

Solutions of the present invention are preferably prepared by adding the salts in the foregoing proportions to water and heating the resultant mixture until all of the salts have been dissolved. The solution is then cooled and filtered to remove impurities. The resulting solution is colorless and stable even at low temperatures and after long periods of storage.

The preferred formulation of this invention is a mixture in which calcium chloride furnishes 20% of the calcium ions by weight, calcium levulinate furnishes 40% by weight and calcium lactate furnishes 40% by weight. This specific combination after extensive testing has been determined to provide optimum results in the treatment of dairy cows suffering from the above noted milk fever symptoms.

In accordance with the present invention it has been determined that superior results are achieved in the treatment of ruminant animals suffering from milk fever symptoms by intravenous administration of the preparations of the present invention if they are free of sugars such as glucose or dextrose, free of boron compounds and free of magnesium compounds. These ingredients, which are usually present in commercially available preparations, have been found to be unnecessary or to cause undesirable complications, or both.

It will be appreciated by those skilled in the art that the preparation of this invention can be modified by the addition thereto in minor amounts of calcium acetate, calcium chlorate, calcium gluconate or calcium propionate without departing from the spirit of the invention While the foregoing discussion has contemplated the use of water as a preferred vehicle, or pharmaceutically acceptable base, for carrying the mixture of calcium salts of the present invention it will be apparent to those skilled in the art that other bases might be employed. Other modifications falling within the purview of the invention will also be apparent to those skilled in the art.

The following examples illustrate the principles and practice of the present invention.

EXAMPLE 1

A mixture consisting of 42.2 grams calcium lactate, 42.2 grams calcium levulinate and 8.32 grams calcium chloride was dissolved in 1000 cc's of QS water by heating and stirring. When all of the salts were completely dissolved, the solution was cooled and filtered. The solution was administered to 83 dairy cows having milk fever symptoms. The solution was administered intravenously in doses of 1000 cc's. Sixty-four of the cows got up without relapse after a single treatment and recovered fully. Ten of the cows recovered after two or more treatments. Nine of the cows failed to recover after treatment.

A group of 147 dairy cows suffering from milk fever symptoms was treated under similar controlled conditions with the largest selling commercially available formulation for treatment of milk fever, which was a solution determined to contain calcium borogluconate, dextrose, magnesium and phosphorus compounds. Of these cows 111 recovered after one or more treatments of the solution by intravenous injection (76%). Thirty-six cows either died or had to be disposed of (24%). Thus the death rate of patients treated with the preparation of the present invention was considerably less than half that experienced with the leading commercially available preparation.

EXAMPLE 2

To 500 cc's distilled water were added enough calcium compounds to provide 7 grams of dissolved calcium ions. This consisted of sufficient calcium chloride to provide 2.1 grams of calcium ions, calcium lactate to provide 1.4 grams of calcium ions and calcium levulinate to provide 3.5 grams of calcium ions. The weight percentages of the calcium ions were thus provided in the ratio of 30% from calcium chloride, 20% from calcium lactate and 50% from calcium levulinate. The mixture was formed into a solution by heating the mixture and was subsequently filtered to remove impurities. The resulting solution was colorless and stable and could be autoclaved. The solution was intravenously administered to a dairy cow which had been diagnosed as suffering from hypocalcemia. The patient rapidly recovered after administration of the solution.

EXAMPLE 3

To 500 cc's distilled water were added enough calcium compounds to provide 7 grams of dissolved calcium ions. This consisted of sufficient calcium chloride to provide 2.1 grams of calcium ions, calcium lactate to provide 3.5 grams of calcium ions and calcium levulinate to provide 1.4 grams of calcium ions. The weight percentages of the calcium ions were thus provided in the ratio of 30% from calcium chloride, 50% from calcium lactate and 20% from calcium levulinate. The mixture was formed into a solution by heating the mixture and was subsequently filtered to remove impurities. The resulting solution was colorless and stable and could be autoclaved. The solution was suitable for intravenous administration to cattle suffering from hypocalcemia.

EXAMPLE 4

To 500 cc's distilled water were added enough calcium compounds to provide 7 grams of dissolved calcium ions. This consisted of sufficient calcium chloride to provide 0.7 grams of calcium ions, calcium lactate to provide 3.15 grams of calcium ions and calcium levulinate to provide 3.15 grams of calcium ions. The weight percentages of the calcium ions were thus provided in the ratio of 10% from calcium chloride, 45% from calcium lactate and 45% from calcium levulinate. The mixture was formed into a solution by heating the mixture and was subsequently filtered to remove impurities. The resulting solution was colorless and stable and could be autoclaved. The solution was administered to a dairy cow which had been diagnosed as suffering from hypocalcemia. The patient rapidly recovered after administration of the solution.

EXAMPLE 5

To 500 cc's distilled water were added enough calcium compounds to provide 7 grams of dissolved calcium ions. This consisted of sufficient calcium chloride to provide 0.7 grams of calcium ions, calcium lactate to provide 2.1 grams of calcium ions and calcium levulinate to provide 4.2 grams of calcium ions. The weight precentages of the calcium ions were thus provided in the ratio of 10% from calcium chloride, 30% from calcium lactate and 60% from calcium levulinate. The mixture was formed into a solution by heating the mixture and was subsequently filtered to remove impurities. The resulting solution was colorless and stable and could be autoclaved. The solution was administered to a dairy cow which had been diagnosed as suffering from hypocalcemia. The patient rapidly recovered after administration of the solution.

EXAMPLE 6

To 500 cc's distilled water were added enough calcium compounds to provide 7 grams of dissolved calcium ions. This consisted of sufficient calcium chloride to provide 0.7 grams of calcium ions, calcium lactate to provide 4.2 grams of calcium ions and calcium levulinate to provide 2.1 grams of calcium ions. The weight percentages of the calcium ions were thus provided in the ratio of 10% from calcium chloride, 60% from calcium lactate and 30% from calcium levulinate. The mixture was formed into a solution by heating the mixture and was subsequently filtered to remove impurities. The resulting solution was colorless and stable and could be autoclaved. The solution was administered to a dairy cow which had been diagnosed as suffering from hypocalcemia. The patient rapidly recovered after administration of the solution.

EXAMPLE 7

To 500 cc's distilled water were added enough calcium compounds to provide 7 grams of dissolved calcium ions. This consisted of sufficient calcium chloride to provide 1.5 grams of calcium ions, calcium lactate to provide 2.75 grams of calcium ions and calcium levulinate to provide 2.75 grams of calcium ions. The weight percentages of the calcium ions were thus provided in the ratio of 21.4% from calcium chloride, 39.3% from calcium lactate and 39.3% from calcium levulinate. The mixture was formed into a solution by heating the mixture and was subsequently filtered to remove impurities. The resulting solution was administered to a dairy cow which had been diagnosed as suffering from hypocalcemia. The patient rapidly recovered after administration of the solution.

What is claimed is:

1. An aqueous solution containing from about 7 to 28 grams of dissolved calcium per 1000 cc in the form of a water soluble mixture of calcium chloride, calcium lactate and calcium levulinate, wherein 10% to 30% of the dissolved calcium is provided by calcium chloride, 20% to 60% thereof by calcium lactate and 20% to 60% thereof by calcium levulinate.

2. A method of treating milk fever and downer cow syndromes in cattle comprising administering by intravenous injection a therapeutically effective dose of an aqueous solution containing from 7 to 28 grams of dissolved calcium per 500 cc's in the form of a water soluble mixture of calcium chloride, calcium lactate and calcium levulinate, in such proportions that the calcium chloride provides from about 10 percent to about 30 percent of the calcium, the calcium lactate provides from about 20 percent to about 60 percent of the calcium, and the calcium levulinate provides from about 20 percent to about 60 percent of the calcium.

3. A pharmaceutical preparation which is free of sugar, boron compounds and magnesium compounds useful for the treatment of animals by intravenous administration comprising a pharmaceutically acceptable base and mixture of calcium chloride, calcium lactate and calcium levulinate in effective amounts sufficient to provide at least about 7 grams of calcium ions when in solution, and the proportions of calcium chloride, calcium lactate and calcium levulinate being such that 10 percent to 30 percent of the calcium ions are provided by the calcium chloride, 20 percent to 60 percent of the calcium ions are provided by the calcium lactate and 20 percent to 60 percent of the calcium ions are provided by the calcium levulinate.

4. An aqueous solution comprising calcium chloride, calcium lactate and calcium levulinate, with said solution containing from about 7 to 28 grams of calcium ion per 500 cc, and wherein the parameters are calcium chloride—10 percent to 30 percent of the calcium ion, calcium lactate—20 percent to 60 percent of the calcium ion, and calcium levulinate—20 percent to 60 percent of the calcium ion.

5. A pharmaceutical composition for treating animals suffering with hypocalcemia and hypophosphatemia, comprising a mixture of calcium chloride, calcium lactate and calcium levulinate in such amounts as to provide about 14 grams of calcium ion when in aqueous solution, and wherein the proportions of calcium chloride, calcium lactate and calcium levulinate are such that the calcium chloride provides approximately 10 percent to 30 percent of the calcium ion, the calcium lactate provides approximately 20 percent to 60 percent of the calcium ion, and the calcium levulinate provides approximately 20 percent to 60 percent of the calcium ion.

6. A pharmaceutical composition for treating milk fever and downer cow syndromes in cattle comprising a water soluble mixture of calcium chloride, calcium lactate and calcium levulinate in such amounts as to provide from 7 to 28 grams of dissolved calcium per 500 cc's of aqueous solution, with the calcium chloride, calcium lactate and calcium levulinate being in such proportions in said mixture that the calcium chloride provides from about 10 percent to about 30 percent of the calcium, the calcium lactate provides from about 20 percent to about 60 percent of the calcium, and the calcium levulinate provides from about 20 percent to about 60 percent of the calcium.

7. A method for treating animals suffering with hypocalcemia and hypophosphatemia comprising administering intravenously a pharmaceutical preparation containing a pharmaceutically acceptable base and an effective amount of at least about 7 grams of dissolved calcium ions, said pharmaceutical preparation comprising a mixture of calcium chloride, calcium lactate and calcium levulinate in solution in such proportions that 10 percent to 30 percent of the calcium ions are provided by the calcium chloride, 20 percent to 60 percent of the calcium ions are provided by the calcium lactate and 20 percent to 60 percent of the calcium ions are provided by the calcium levulinate, said pharmaceutical preparation being free of sugar, boron compounds and magnesium compounds.

8. A method of treating milk fever and downer cow syndromes in cattle comprising administering by intravenous injection a therapeutically effective dose of an aqueous solution containing from 7 to 28 grams of dissolved calcium per 1000 cc's in the form of a water soluble mixture of calcium chloride, calcium lactate and calcium levulinate, in such proportions that the calcium chloride provides from about 10 percent to about 30 percent of the calcium, the calcium lactate provides from about 20 percent to about 60 percent of the calcium, and the calcium levulinate provides from about 20 percent to about 60 percent of the calcium.

9. A pharmaceutical composition for treating milk fever and downer cow syndromes in cattle comprising a water soluble mixture of calcium chloride, calcium lactate and calcium levulinate in such amounts as to provide from 7 to 28 grams of dissolved calcium per 1000 cc's of aqueous solution, with the calcium chloride, calcium lactate and calcium levulinate being in such proportions in said mixture that the calcium chloride provides from about 10 percent to about 30 percent of the calcium, the calcium lactate provides from about 20 percent to about 60 percent of the calcium, and the calcium levulinate from about 20 percent to about 60 percent of the calcium.

10. A method for treating animals suffering with hypocalcemia and hypophosphatemia comprising administering intravenously an aqueous solution containing from about 7 to about 28 grams of dissolved calcium ion per 1,000 cc's, said aqueous solution comprising a mixture of calcium chloride, calcium lactate and calcium levulinate in solution in such proportions that the calcium chloride provides about 10 percent of the calcium ions, the calcium lactate provides about 45 percent of the calcium ions, and the calcium levulinate provides about 45 percent of the calcium ions.

11. A pharmaceutical composition for treating animals suffering with hypocalcemia and hypophosphatemia, comprising a mixture of calcium chloride, calcium lactate and calcium levulinate in such amounts as to provide about 7 to about 28 grams of calcium ion per 1000 cc's when in aqueous solution, with the proportions of calcium chloride, calcium lactate and calcium levulinate being such that calcium chloride provides about 10 percent of the calcium ion, the calcium lactate provides about 45 percent of the calcium ion and the calcium levulinate provides about 45 percent of the calcium ion.

12. An aqueous solution comprising calcium chloride, calcium lactate and calcium levulinate, with said solution containing from about 7 to 28 grams of calcium ion per 1,000 cc's, and wherein 10 percent of the calcium ion in said solution is provided by calcium chloride, 45 percent of the calcium ion is provided by calcium lactate and 45 percent of the calcium ion is provided by calcium levulinate.

* * * * *